United States Patent
Clarke

Patent Number: 5,632,743
Date of Patent: May 27, 1997

[54] METHOD OF THAWING CRYOSURGICAL APPARATUS

[75] Inventor: Brian K. R. Clarke, Oakwood, England

[73] Assignee: Spembly Cryosurgery Limited, Hampshire, England

[21] Appl. No.: 232,281

[22] PCT Filed: Nov. 3, 1992

[86] PCT No.: PCT/GB92/02030

§ 371 Date: May 31, 1994

§ 102(e) Date: May 31, 1994

[87] PCT Pub. No.: WO93/08752

PCT Pub. Date: May 13, 1993

[30] Foreign Application Priority Data

Nov. 5, 1991 [GB] United Kingdom ............... 9123413

[51] Int. Cl.⁶ ........................................... A61B 17/36
[52] U.S. Cl. ................ 606/24; 606/20; 606/23; 128/898
[58] Field of Search ................ 606/20–26; 607/104, 607/105; 128/898

[56] References Cited

U.S. PATENT DOCUMENTS

| | | | |
|---|---|---|---|
| Re. 28,657 | 12/1975 | Barger et al. | 606/23 |
| 3,613,689 | 10/1971 | Crump et al. | 606/23 |
| 4,018,227 | 4/1977 | Wallach | 606/23 |
| 4,063,560 | 12/1977 | Thomas et al. | |
| 4,206,760 | 6/1980 | Davis | |
| 4,275,734 | 6/1981 | Mitchiner et al. | 606/23 |
| 4,278,090 | 7/1981 | Van Gerven | 606/23 |
| 4,280,499 | 7/1981 | Squazzi | |
| 4,348,873 | 9/1982 | Yamauchi et al. | 606/20 X |
| 4,377,168 | 3/1983 | Rzasa et al. | |
| 4,519,389 | 5/1985 | Gudkin et al. | |
| 4,946,460 | 8/1990 | Merry et al. | |
| 5,108,390 | 4/1992 | Potocky et al. | 606/21 |
| 5,224,943 | 7/1993 | Goddard | 606/20 |

FOREIGN PATENT DOCUMENTS

| | | |
|---|---|---|
| 86-086863/14 | 6/1983 | U.S.S.R. |
| 1217377 | 3/1986 | U.S.S.R. |
| 86-296896/45 | 3/1986 | U.S.S.R. |
| WO83/03961 | 11/1983 | WIPO |

*Primary Examiner*—Angela D. Sykes
*Assistant Examiner*—Michael Peffley
*Attorney, Agent, or Firm*—W. Thad Adams, III, P.A.

[57] ABSTRACT

A method of thawing of cryosurgical apparatus, and in particular a cryosurgical probe, subsequent to a freezing process involves the interuption of the cryogen supply to the probe followed by the introduction of a warmed inert gas. The gas is circulated within the probe cryogen circulation system to affect thawing of the apparatus so that the probe may easily be withdrawn from the body. The gas, which may be nitrogen, is preferably passed through a heat exchange arrangement before being introduced into the probe.

4 Claims, 1 Drawing Sheet

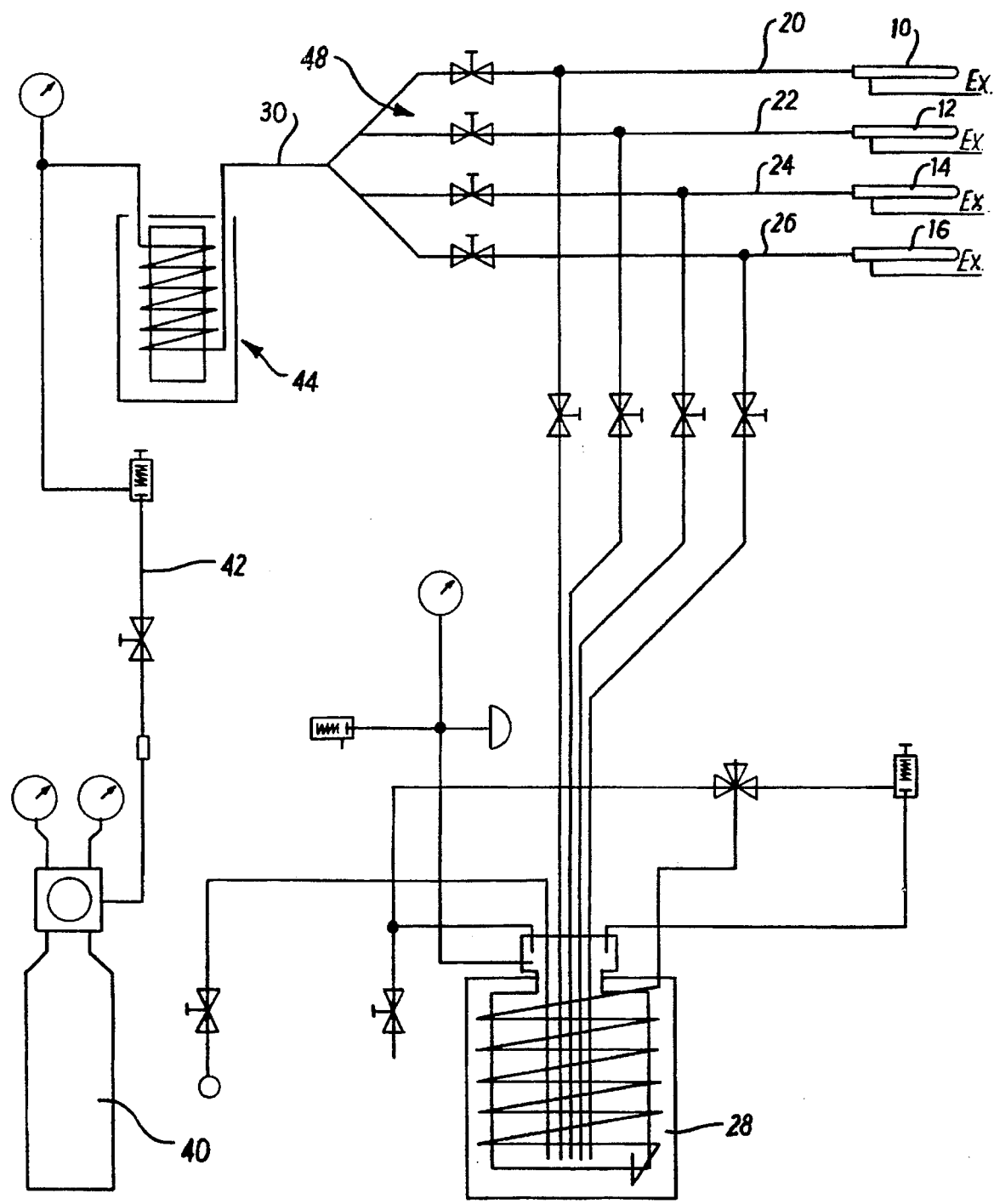

METHOD OF THAWING CRYOSURGICAL APPARATUS

This application is a national stage application, according to Chapter II of the Patent Cooperation Treaty. This application claims the priority dates of Nov. 5, 1991, U.K. Patent No. 9123413.8.

The invention concerns cryosurgical apparatus, and relates in particular to a method of thawing a cryosurgical probe subsequent to carrying out a freezing process, in order that the probe may be withdrawn.

Following an operation involving the destruction of tumourous tissue by freezing with a cooled probe inserted into the body, it is necessary to thaw or allow to be thawed the tissue immediately surrounding the probe in order that the latter may be withdrawn. Such thawing is commonly carried out by one of two principal methods. The first involves the use of latent body heat. This has the serious disadvantage that the process is extremely slow, thereby significantly increasing operation times. The second method utilises electrical heating of the probe tip. Although this is a considerably faster method, there are inherent safety problems which necessitate the utmost care in producing and using equipment of this kind.

The invention seeks to mitigate or obviate the above mentioned difficulties by providing a relatively fast yet safe method of raising the temperature of the probe tip on completion of an operation.

According to the invention there is provided a method of thawing cryosurgical apparatus of a type wherein a liquid cryogen is supplied to the apparatus through a first path of an internal circulation system thereof to a tip area to effect cooling thereof by vaporisation of the cryogen and the resultant cryogen gas is removed from the apparatus through a second path of the internal circulation system, in which method the supply of cryogen to the apparatus is interrupted when surgery is complete, whereupon a supply of an inert gas is provided, the latter is heated to a required predetermined temperature, and the heated inert gas is circulated through the first and second paths of the circulation system to effect thawing of the apparatus.

The method is particularly suited to liquid nitrogen cooled probes, such as the kind in which the cryogen is delivered to the probe tip via a delivery tube located along the probe axis and returned via an annular gap within the probe housing surrounding the delivery tube.

Preferably the inert gas is nitrogen. The gas may be heated by feeding it to the apparatus via a heat exchanging arrangement.

BRIEF DESCRIPTION OF THE DRAWING

The invention will be described in more detail by way of example only with reference to the accompanying drawing which is a schematic block diagram showing a cryosurgical probe arrangement for utilising the thawing method of the invention.

The figure shows an arrangement containing four cryosurgical probes 10, 12, 14 and 16. Each probe is connected by a delivery line 20, 22, 24 and 26 to a supply vessel 28 of a liquid cryogen, such as liquid nitrogen.

The lines 20, 22, 24 and 26 are also in communication with a further delivery line 30 as described in more detail hereinafter.

The system provides a supply 40 of an inert gas, in the present example, nitrogen. Gas may be supplied through a delivery line 42 to a heat exchanging arrangement 44, and thus to the cryogen circulation systems of the probes 10, 12, 14 and 16 via the line 30 and the lines 20, 22, 24 and 26.

Each of the probes 10, 12, 14 and 16 may be supplied with the cryogen from the supply vessel 28 in any convenient manner, such as via a delivery tube located along the respective probe longitudinal axis, as is well known in the art. Following the freezing of the probe tip, the cryogen is then removed, for example via an annular gap within a housing of the probe surrounding the delivery tube, to a suitable exhaust line on the probe.

When the operation is complete and it is required to withdraw the probe, the supply of cryogen from the vessel 28 is shut off by means of a suitable valve arrangement. Gas is passed from the supply 40 through the line 42 to the heat exchanger 44. On passing through the heat exchanger, the gas is warmed to the required predetermined temperature. From the heat exchanger 44 the gas supply is passed through the line 30 and then via suitable valve systems 48 to the supply line of the appropriate probe. The warmed nitrogen is thereby circulated through the probe body and tip whereby it provides localised heat within the probe tip. The gas may then be exhausted through the existing probe cryogen outlet lines.

Any cryogen remaining within the probe circulation system is automatically purged by the incoming gas supply.

It will be appreciated that control and monitoring of the apparatus can be achieved by the incorporation of any appropriate valves, gauges, regulators or other instrumentation as is well known to the person skilled in the art. Such systems are not therefore described in detail herein.

There is therefore described a particularly convenient way of raising the temperature of the probe body. The method naturally permits suitable control of the speed of the thawing process by appropriate adjustments to the gas supply. The use of nitrogen gas in the given example also obviates problems of the formation of ice deposits within the cryogen circulation system on re-cooling which could arise if, for example, a liquid was used as the purging and heat transfer medium.

I claim:

1. A method of thawing a cryosurgical apparatus, comprising the steps of:

(a) supplying a liquid cryogen to the apparatus through a first path of an internal circulation system thereof to a tip area to effect cooling thereof by vaporization of the liquid cryogen;

(b) interrupting the supply of cryogen to the apparatus when surgery is complete;

(c) after (b), injecting a heated inert gas of predetermined temperature through the first path of the internal circulation system, and purging the cryogen gas remaining in the apparatus through a second path of the internal circulation system;

(d) circulating the heated inert gas through the first and second paths of the circulation system to effect thawing of the apparatus; and (e) exhausting the heated inert gas from the apparatus through the second path of the internal circulation system.

2. A method according to claim 1, wherein the step of injecting heated inert gas comprises the step of injecting nitrogen through the first path of the internal circulation system.

3. A method according to claim 1, wherein the step of injecting heated inert gas comprises the step of providing a heat exchanging arrangement for heating the inert gas prior to passage through the first path of the internal circulation system.

4. A method according to claim 1, and comprising the steps of providing a delivery tube located along a probe axis for supplying the inert gas to the tip area of the apparatus.

* * * * *